United States Patent [19]

Feitler

[11] Patent Number: 4,612,387

[45] Date of Patent: Sep. 16, 1986

[54] PRODUCTION OF CARBOXYLIC ACIDS AND ESTERS

[75] Inventor: David Feitler, Whitehall, Pa.

[73] Assignee: Air Products and Chemicals, Inc., Allentown, Pa.

[21] Appl. No.: 336,820

[22] Filed: Jan. 4, 1982

[51] Int. Cl.⁴ .................. C07C 1/20; C07C 51/12; C07C 67/36

[52] U.S. Cl. .................. 560/232; 560/241; 562/517; 562/519; 585/640; 585/733

[58] Field of Search ............... 585/640, 733; 560/232, 560/204, 114; 562/519, 517, 497

[56] References Cited

U.S. PATENT DOCUMENTS

| | | | |
|---|---|---|---|
| 1,920,373 | 8/1933 | Gosselin | 260/112 |
| 3,689,533 | 9/1972 | Schultz | 560/232 |
| 3,702,886 | 11/1972 | Argauer et al. | 423/328 |
| 3,717,670 | 2/1973 | Schultz | 560/105 |
| 3,894,106 | 7/1975 | Chang et al. | 260/668 R |
| 3,894,107 | 7/1975 | Butter et al. | 260/668 R |
| 3,928,483 | 12/1975 | Chang et al. | 260/668 R |
| 4,011,278 | 3/1977 | Plank et al. | 260/682 |
| 4,013,732 | 3/1977 | Chang et al. | 260/668 R |
| 4,066,714 | 1/1978 | Rodewald | 260/682 |
| 4,083,888 | 4/1978 | Caesar et al. | 260/682 |
| 4,134,912 | 1/1979 | Naglieri et al. | 562/579 |
| 4,139,600 | 2/1979 | Rollmann et al. | 423/329 |
| 4,229,424 | 10/1980 | Kokotailo | 423/328 |

OTHER PUBLICATIONS

CA 93:45920m.
J. B. Nagy et al. in J. Mol. Cat., 5 (1979), 393-397.
C. D. Chang and A. J. Silvestri in J. Cat., 45 (1977), 249-259.
C. D. Chang et al. in J. Catal. 56 (1979), 169-173.

Primary Examiner—Vivian Garner
Attorney, Agent, or Firm—Michael Leach; James C. Simmons; E. Eugene Innis

[57] ABSTRACT

A method for making monocarboxylic acids and esters comprising contacting carbon monoxide and a monohydric alcohol containing 1 to 4 carbon atoms in the presence of a crystalline aluminosilicate zeolite having a silica to alumina ratio at least about 6 and a constraint index within the approximate range of 1 to 12 under a pressure of at least one atmosphere. Also coproduced are hydrocarbons, particularly ethylene and "gasoline".

20 Claims, No Drawings

PRODUCTION OF CARBOXYLIC ACIDS AND ESTERS

TECHNICAL FIELD

This invention relates to a process for the preparation of carboxylic acids and esters. More particularly, it relates to a process for the reaction of monohydric alcohols and carbon monoxide in the presence of a catalyst to yield carboxylic acids and esters.

BACKGROUND OF THE INVENTION

Carbonylation processes are old in the art as exemplified by U.S. Pat. No. 1,920,373 which discloses the reaction between carbon monoxide and water in the presence of catalytic substances with a zeolitic structure to produce oxygen containing aliphatic compounds. Also well known are the carbonylation processes for the preparation of carboxylic acids from alcohols and especially the production of acetic acid by the carbonylation of methanol.

The prior art teaches the use of a number of catalysts for the synthesis of carboxylic acids by reaction of alcohols with carbon monoxide at elevated temperatures and pressures in both gas phase fixed bed reactions and liquid phase reactions. Catalysts such as phosphoric acid, phosphates, heavy metal salts such as zinc and cuprous chlorides, silicates of various metals, and boron trifluoride in various hydration states have been reported to function for the production of acetic acid by reaction of methyl alcohol and carbon monoxide at elevated temperatures and pressures of the order of 400° C. and 10,000 psig, respectively. Somewhat less severe reaction conditions of temperature and/or pressure have been reported in the literature employing specific catalyst compositions, e.g., 330° to 340° C. using liquid phosphoric acid containing copper phosphate; 300° to 500° C., and 2,000 to 4,000 psig using active charcoal impregnated with phosphoric acid; and 260° to 360° C. and 2,800 to 5,000 psig using metal carbonyls, such as iron, cobalt and nickel, in conjunction with their halides or free halogens in the liquid phase.

In addition, U.S. Pat. No. 2,019,754 discloses the reaction of aliphatic alcohols and carbon monoxide in the vapor phase in the presence of a catalyst which is a gaseous adsorbent, such as the adsorbent oxides of aluminum, silicon, magnesium, titanium, zirconium and tungsten.

U.S. Pat. Nos. 3,689,533 and 3,717,670 are representative of the prior art preparation of carboxylic acids and esters by the reaction of alcohols and carbon monoxide in the presence of a supported catalyst comprising a rhodium component and a halide promoter. Included in the extensive listing of suitable support, or carrier, materials for the rhodium catalyst are "zeolites as well as the zeolitic molecular sieves".

U.S. Pat. No. 4,134,912 discloses the preparation of acetic acid by the carbonylation of methanol using an iodide and a nickel catalyst in the presence of a tin promoter.

CA 93:45920m discloses that NaX zeolite containing 0.2 to 0.5% rhodium promoted with iron, copper, cobalt and nickel oxides catalyzed the preparation of methyl acetate with 90 to 94% selectivity by carbonylating methanol at 180° to 230° and 1 atmosphere.

J. B. Nagy, et al. in J. MOL. CAT., 5 (1979) 393-397 describe the $^{13}$C-nmr investigation of the conversion of methanol, in the presence of carbon monoxide, on H-ZSM-5 zeolite. The methanol was contacted with carbon monoxide at a pressure of 130 torr. It is stated that the presence of carbon monoxide has little effect on the conversion of methanol although some carbon monoxide is incorporated into the products. Carboxylic group containing products were not detected by $^{13}$C-nmr.

C. D. Chang and A. J. Silvestri in J. Cat. 47 (1977) 249-259 describe the conversion of numerous compounds besides methanol to hydrocarbons using ZSM-5 type catalysts. Carbonyl containing compounds including acetone, acetic acid, n-propyl acetate and n-butyl formate were converted.

Currently, the commercially practiced art which uses a rhodium catalyst and a halide promoter for the synthesis of acetic acid from methanol and carbon monoxide has a number of problems and deficiencies. Capital and operating costs due to the use of a homogeneous rhodium catalyst are one example. The use of a rhodium catalyst process necessitates a supply of catalyst makeup in addition to the catalyst charge and also requires catalyst recovery and recycle equipment. The use of an iodide containing promoter in the acetic acid process requires an iodide charge and makeup, and recycle equipment. Additionally, the use of iodide renders the system extremely corrosive requiring expensive and exotic materials of construction. Further, the presence of water in the liquid reaction medium leads to complicated and expensive product separations.

A catalyst which has become increasingly important in numerous catalyzed processes is the crystalline zeolite ZSM-5 disclosed in U.S. Pat. No. 3,702,866. It is well known that ZSM-5 and ZSM-5 type crystalline zeolites are very useful in the conversion of methanol or its derivatives to hydrocarbons, particularly gasoline. Representative of such art are U.S. Pat. Nos. 3,894,106; 3,894,107; 3,928,483; 4,011,278; 4,013,732; 4,066,714; 4,083,888; 4,139,600; and 4,229,422.

C. D. Chang, et al. in J. CATAL. 56 (1979) 169-173, teach that the ZSM-5 type zeolites reversably convert methanol to dimethyl ether as the initial step in the reaction sequence to the production of hydrocarbons.

SUMMARY OF THE INVENTION

According to the invention, a method has been discovered for the preparation of monocarboxylic acids and esters from a $C_1$–$C_4$ monohydric alcohol and carbon monoxide. The method comprises contacting carbon monoxide and the monohydric alcohol with a catalyst comprising a crystalline aluminosilicate zeolite having a silica to alumina ratio of at least about 6 and a constraint index within the approximate range of 1 to 12, under a pressure of at least 1 atmosphere and at a temperature sufficient to effect a reaction between the carbon monoxide and the monohydric alcohol to produce a monocarboxylic acid or ester.

By the process of this invention, $C_1$–$C_4$ monohydric alcohols yield monocarboxylic acids containing an additional carbon atom. Representative $C_1$–$C_4$ alcohols are methanol, ethanol, the propanols and the butanols. The products of the reaction are acetic acid, propionic acid, the butyric acids and the valeric acids and their corresponding esters. In the preferred embodiment of the invention, carbon monoxide and methanol are contacted to afford acetic acid and/or methyl acetate.

The process of this invention has several advantages in addition to the production of monocarboxylic acids and esters in significant conversions and selectivities.

The process obviates the need for a homogeneous catalyst recycle system by eliminating the need for a rhodium catalyst. Because a halide promoter is no longer required, exotic materials of construction are no longer necessary. Other features of the process include operativeness at relatively low pressures, practical rates of reaction, low recycle ratios (higher conversion per pass), and good catalyst lifetimes.

Hydrocarbons, such as ethylene and "gasoline", are by-products in the production of the carboxylic acid and/or ester. Accordingly, the process of this invention has several advantages in coproduction schemes wherein ethylene or liquid fuels are produced as coproducts. In particular, coproduction of acetic acid and ethylene in molar ratios between 0.25 and 2 may be notably useful for the ultimate production of polyvinyl acetate and polyvinyl alcohol from synthesis gas. Current proposals for the preparation of these materials require various noble-metal catalyzed carbonylation and reduction steps promoted by a halide. These schemes conform to an overall stoichiometry of $$2MeOH + 2CO + H_2 \rightarrow CH_3CO_2CH=CH_2 + 2H_2O \quad (1)$$

to produce vinyl acetate, and further steps of $$CH_3CO_2CH=CH_2 \rightarrow \text{polyvinyl acetate} \quad (2)$$

$$\text{polyvinyl acetate} + MeOH \rightarrow \text{polyvinyl alcohol} + CH_3CO_2CH_3 \quad (3)$$

to produce usable polymers. Equation (3) shows a requirement for these processes to export acetic acid.

It is known to react acetic acid and ethylene in the presence of oxygen to produce vinyl acetate.

$$CH_3CO_2H + C_2H_4 + \tfrac{1}{2}O_2 \rightarrow CH_3CO_2CH=CH_2 \quad (4)$$

The invention of this disclosure:

$$3MeOH + CO \rightarrow \sim 1C_2H_4 + 1CH_3CO_2H + 2H_2O \quad (5)$$

allows for production of a mixture of ethylene and acetic acid where less acetic acid than ethylene is produced and the ratio brought to 1 by the recycle of acetic acid produced by hydrolysis of polyvinyl acetate. This invention, therefore, is essential to synthesis gas-based polyvinyl acetate and polyvinyl alcohol production if export of acetic acid is prohibitive.

DETAILED DESCRIPTION OF THE INVENTION

It has been found that contacting carbon monoxide and methanol with a particular class of zeolite catalysts affords the production of acetic acid or its methyl ester, or both, in contrast to the teaching of the J. B. Nagy, et al. reference. The reaction of carbon monoxide and a $C_1$–$C_4$ monohydric alcohol, preferably methanol, is performed in the presence of a crystalline aluminosilicate zeolite having a silica to alumina ratio of at least about 6, preferably to about 150, and a constraint index within the approximate range of 1 to 12. While the reaction can be performed at any temperature sufficient to effect a reaction between the carbon monoxide and the alcohol, the preferred operating temperature lies in the range of about 200° to 600° C. Although any pressure of about 1 atmosphere or greater can be used, a desirable pressure range is from about 100 to 50,000 psig (8 to 3,400 atm) and preferably to about 20,000 psig (1,360 atm). A more preferred pressure range is from about 500 to 3,000 psig (35 to 205 atm). Inert gases such as nitrogen, argon and the like may be included in the system. Useful space velocities (WHSV) for the reaction of alcohol range from about 0.01 to 10 grams alcohol/grams catalyst/hour. The carbon monoxide:alcohol molar feed ratio ranges from about 1:1 to 1,000:1, preferably about 10:1 to 100:1.

The $C_1$–$C_4$ monohydric alcohol, especially methanol, may be introduced into the reaction zone by itself or as a mixture with water. When diluted with water, the volume percent alcohol may range from about 0.1% to nearly 100% with the preferred range being from about 10% to 50%.

Contemplated as the functional equivalent of a $C_1$–$C_4$ monohydric alcohol as a reactant with carbon monoxide in the process of this invention in this specification and the appended claims is its ether derivative. Specifically, dimethyl ether is the functional, or operative, equivalent of methanol.

The crystalline aluminosilicate zeolites suitable for use in the process of this invention include not only those zeolites possessing X-ray crystallinity but also those which show X-ray amorphism but possess infrared crystallinity as disclosed in P. A. Jacobs, et al., J.C.S. CHEM. COMM., 1981, 591–593, which is incorporated by reference.

The aluminosilicate zeolites useful in the process are members of a class exhibiting some unusual properties. These zeolites induce transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type.

Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by ten-membered rings of oxygen atoms. It is to be understood, of course, that these rings are those formed by the regular disposition of the tetrahedra making up the anionic framework of the crystalline alumina silicate, the oxygen atoms themselves being bonded to the silicon or aluminum atoms at the centers of tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight-membered rings of oxygen atoms, then access by molecules of larger cross-section than normal hexane is excluded and the zeolite is not of the desired type. Windows of ten-membered rings are preferred although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite for shape selective reactions. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite in the form of pellets or extrudate, is crushed to a particle size about that of coarse sand and mounted in a glass tube. Prior to testing, the zeolite is treated with a stream of air at 1,000° F. (538° C.) for at least 15 minutes. The zeolite is then flushed with helium and the temperature adjusted between 550° and 950° F. (288° and 510° C.) to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present intention are those having a constraint index in the approximate range of 1 to 12. Constraint Index (CI) values for some typical zeolites are given in Table I.

TABLE I

| CRYSTALLINE ALUMINOSILICATE | CONSTRAINT INDEX |
| --- | --- |
| ZSM-5 | 8.3 |

TABLE I-continued

| CRYSTALLINE ALUMINOSILICATE | CONSTRAINT INDEX |
| --- | --- |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforementioned range of 550° to 950° F. (288° to 510° C.), with accompanying conversion between 10% and 60%, the constraint index may vary within the indicated approximate range of 1 to 12. Likewise, other variables such as the crystal size of the zeolite, the presence of possible occluded contaminents and binders intimately combined with the zeolite may effect the constraint index. It will accordingly be understood by those skilled in the art that the constraint index, as utilized herein, while affording a highly useful means for characterizing of the zeolites of interest is approximate, taking into consideration the manner of its determination, with the probability, in some instances, of compounding variable extremes. However, in all instances, at a temperature within the above mentioned range of 550° to 950° F. (288° to 510° C.), the constraint index will have a value for a given zeolite of interest herein within the approximate range of 1 to 12.

The class of zeolites which has been defined is exemplified by ZSM-5, ZSM-11, ZSM-12, ZSM-35 and ZSM-38 and other similar materials. U.S. Pat. No. 3,702,886 describing ZSM-5 is incorporated by reference.

ZSM-11 is more particularly described in U.S. Pat. No. 3,709,979 which is incorporated by reference.

ZSM-12 is more particularly described in U.S. Pat. No. 3,832,449 which is incorporated by reference.

ZSM-35 is more particularly described in U.S. Pat. No. 4,016,245 which is incorporated by reference.

ZSM-38 is more particularly described in U.S. Pat. No. 4,046,859 which is incorporated by reference.

ZSM-43 is more particularly described in U.S. Pat. No. 4,209,499 which is incorporated by reference.

ZSM-48 is more particularly described in European Patent Application No. 80302113.8, Publication No. 0 023 089 A1 which is incorporated by reference.

A crystalline aluminosilicate zeolite product having a structure intermediate that of ZSM-5 and ZSM-11 is more particularly described in U.S. Pat. No. 4,229,424 which is incorporated by reference.

The specific zeolites described, when prepared in the presence of organic cations, are catalytically inactive, possibly because the intracrystalline free space is occupied by organic cations from the forming solution. They may be activated by heating in a inert atmosphere at 1,000° F. (538° C.) for one hour, for example, followed by base exchange with ammonium salts followed by calcination at 1,000° F. (538° C.) in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts or aqueous hydrogen chloride followed by calcination in air at about 1,000° F. (538° C.) for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite.

The preferred crystalline aluminosilicates are ZSM-5, ZSM-11, ZSM-12, ZSM-38 and ZSM-35 with ZSM-5 particularly preferred.

Generally, the zeolite, either directly or via initial ammonium or aqueous acid exchange followed by calcination, should be hydrogen exchanged such that a predominant portion of its exchangeable cations are hydrogen ions. In general, it is contemplated that more than 50% and preferably more than 75% of the cationic sites of the crystalline aluminosilicate zeolite will be occupied by hydrogen ions or metal ions other than alkali metal ions.

In addition to the hydrogen form, other forms of the zeolite wherein the original alkali metal has been reduced to less than about 1.5% by weight may be used. Thus, the original alkali metal of the zeolite may be replaced by ion exchange with other suitable metal ions, particularly those capable of forming a carbonyl complex, such as the metal ions of Groups IB, IIB, IVB and VIII of the Periodic Table, including the metal ions of copper, silver, gold, zinc, and manganese. Furthermore, combinations of exchange can be used in which, for example, hydrogen and copper may be exchanged for the alkali metal.

Surprisingly, the aluminosilicate zeolites used in the process of this invention demonstrate improved conversions when ion exchanged with salts of carbonyl complexing transition metals. It is believed that the presence of such transition metals on the internal surface of the zeolite provides a means for adsorbing many more times the amount of carbon monoxide so that the reactive intermediate which is present on the zeolite surface can readily react with a nearby carbon monoxide molecule.

It is prudent to use those transition metal ions which form carbonyl complexes that are relatively stable (non-volatile) under the conversion reaction conditions used. For instance, metal carbonyl compounds of iron, cobalt and nickel form relatively volatile carbonyls and require the use of high partial pressures of carbon monoxide to remain stable under high reaction temperatures. As an example, $Co_2(CO)_8$ requires a partial pressure of carbon monoxide from 3,000 to 10,000 psig (205 to 680 atm) at 175° to 300° C. It is also advisable to use a transition metal in the zeolite catalyst which is not active for the Fischer-Tropsch or water gas shift reactions. As demonstrated in the following examples, copper is the preferred transition metal for ion exchange.

The amount of carbonyl complexing metal ion incorporated in the crystalline aluminosilicate zeolite should be in a metal:aluminum molar ratio ranging from about 1:100 to about 1:1, preferably about 1:10 to 1:2. These metal exchanged zeolites can be prepared readily by one skilled in the art by treating the zeolite with an aqueous salt of the desired metal ion following the techings of U.S. Pat. Nos. 4,034,065 and 4,019,879 showing the production of a copper containing zeolite, which patents are incorporated by reference. Other methods of ion exchange and impregnation of the zeolites are disclosed in U.S. Pat. Nos. 4,278,565 and 4,292,205 which are incorporated by reference.

In a preferred aspect of this invention, the zeolites are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products and should, in the process of this invention, maximize the reaction between the alcohol and carbon monoxide. Therefore, the preferred zeolites of this invention are those having a constraint index of about 1 to about 12, a silica to alumina ratio of at least about 12 and a dried crystal density of not less than about 1.6 grams per cubic centimeter. The dry density for known structures may be calculated from the number of silicon plus aluminum atoms per 1,000 cubic Angstroms, as given, e.g., on Page 19 of the article on Zeolite Structure by W. M. Meier. This paper, which is incorporated by reference, is included in "Proceedings of the Conference on Molecular Seives, London, April 1967," published by the Society of Chemical Industry, London, 1968. When the crystal structure is unknown, the crystal framework density may be determined by clasical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the focus of catalytic activity.

Crystal framework densities of some typical zeolites are shown in Table II.

TABLE II

| Zeolite | Void Volume | Framework Density |
|---|---|---|
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

In practicing the carbonylation process, it may be desirable to incorporate the zeolite in another material resistant to the temperatures and other conditions employed in the process. Such matrix materials include synthetic or naturally occurring substances as well as inorganic materials such as clay, silica and/or metal oxides. The latter may be either naturally occurring or in the form of gelatinous percipitates or gels including mixtures of silica and metal oxides. Naturally occurring clays which can be composited with the zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed may be composited with a porous matrix material, such as alumina, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to 99% by weight and more usually in the range of about 5 to about 80% by weight of the composite.

In practicing the carbonylation process of this invention, the catalyst is preferably used in the reaction zone of a fixed bed reactor with all components entering and leaving the catalyst volume in the vapor phase under effective conversion conditions for alcohol and/or ether conversion. Thus a gas phase fixed bed reaction is preferred although liquid phase reactions are possible.

The alcohol and/or ether conversion process may be carried out as a batch-type, semi-continuous or continuous operation utilizing a fixed or moving bed catalyst system. One embodiment entails use of a catalyst zone in which the alcohol or ether charge is passed concurrently or countercurrently through a moving bed of particle-form catalyst. The catalyst after use is conducted to a regeneration zone in which coke is burned from the catalyst in an oxygen containing atmosphere, e.g. air, at an elevated temperature, after which the regenerated catalyst is recycled to the conversion zone for further contact with the alcohol or ether feed.

EXAMPLE I

An H-ZSM-5 catalyst was prepared according to the teaching of U.S. Pat. Nos. 3,702,886 and 4,011,278. According to a typical preparation, Solution A was prepared containing 3.9 grams sodium hydroxide (NaOH), 68.5 grams tetrapropyl ammonium bromide (TPABr) and 0.3 liters of deionized water. Solution B contained 4.8 grams of sodium meta-aluminate (NaAlO$_2$.3H$_2$O) in 0.3 liters of deionized water. Solution C comprised 115 grams of colloidal silica (30% SiO$_2$ in water). The three solutions were mixed in a one gallon autoclave and stirred for 72 hours at 1,000 rpm at 150° C. After cooling the resulting mixture was decanted and allowed to settle in a glass jar. The zeolite solid was removed from the jar and washed by stirring with two 150 ml portions of deionized water for two hours. After each wash, the solid was separated from the liquid by centrifugation at 2,500 rpm for 30 minutes. After the second wash, the solid was allowed to air dry, then placed in a box furnace at 600° C. overnight. The deammoniated zeolite was converted to its hydrogen form by three 2-hour wash cycles with 150 ml of 5% hydrochloric acid. After drying, the preparation gave 23.7 grams of catalyst A having the following composition:

|  | Wt % |
| --- | --- |
| SiO$_2$ | 84.7 |
| Al$_2$O$_3$ | 13.6 |

The powder diffraction pattern matched all major peaks reported for H-ZSM-5.

Table III shows the analytical data for catalysts A-E prepared by this procedure and the amounts of the ingredients used.

TABLE III

| | CATALYST | | | | |
| --- | --- | --- | --- | --- | --- |
| | A | B | C | D** | E |
| SOLUTION A | | | | | |
| NaOH | 3.9 | 3.9 | 3.9 | 15.6 | 3.9 |
| TPABr | 68.5 | 68.5 | 68.5 | 274 | 68.5 |
| SOLUTION B | | | | | |
| NaAlO$_2$.3H$_2$O | 4.8 | 9.6 | 9.6 | 48 | 14.4 |
| SOLUTION C | | | | | |
| Colloidal Silica | 115 | 115 | 115 | 460 | 115 |
| WEIGHT % | | | | | |
| SiO$_2$ | 84.7 | 83.4 | 85.5 | 88.6 | 81.9 |
| Al$_2$O$_3$ | 13.6 | 5.31 | 12.9 | 4.03 | 5.9 |
| Na$_2$O | 0.11 | 0.73 | — | — | — |
| Cl | — | 0.02 | — | — | 2.46 |
| *Crystallinity | Nearly Amorphous | Medium Crystallinity | Intermediate Crystallinity | Low Crystallinity | Poor |

*These are qualitative estimates based on examination of an x-ray diffraction powder pattern. No quantitive conclusions were drawn.
**One gallon scale preparation.

EXAMPLE II

In this example, the preparation of zeolites impregnated with copper is described. Following the examples of U.S. Pat. Nos. 4,034,065 and 4,019,879, catalyst B of Example I was treated with copper nitrate:

Cu(NO$_3$)$_2$.3H$_2$O (12.08 g) was dissolved in 500 ml of distilled H$_2$O. Catalyst B (10 g) was slurried in 50 ml of distilled water and acidified with acetic acid to between pH 3 and 4. The copper nitrate solution was added (100 cc) and the mixture stirred for one hour, then filtered. This process was repeated two more times. The solids were then slurried and stirred in 100 ml of distilled water for ten minutes. This wash procedure was repeated twice, and the resulting solids air dried at 100° C. to yield catalyst F which contained ~0.26% Cu.

EXAMPLE III

Acetic acid was prepared using a powdered zeolite catalyst of the foregoing Examples as a 10 gram bed of catalyst in a downflow microreactor. Methanol, or a mixture of methanol and water, as a liquid at a rate of between 0.1 and 10 ml/hr mixed with a stream of carbon monoxide, was fed to a preheater to insure vaporization, and the combined stream passed into the reactor. Pressure was maintained at 1,000 psig (69 atm) by a back pressure regulator. Reaction gases were collected downstream of the back pressure regulator and were analyzed by gas chromotography. Liquid samples were collected in a series of liquid nitrogen and dry ice/methylene chloride traps and analyzed by gas chromatography. Mass balances of 60 to 100% were usually achieved. Table IV lists the experimental conditions and observed conversions and selectivities for Runs 1 to 12 performed according to the above procedure.

Runs 5, 7 and 8 were controls to show the limits of the analyses. At concentrations less than $3 \times 10^{-4}$M the analysis proved unreliable. To be conservative, all the data less than $3 \times 10^{-4}$M were shown at this upper bound. Runs 5 and 8 involved contacting carbon monoxide and methanol in the reaction chamber in the absence of an H-ZSM-5 type catalyst, the reaction chamber of Run 8 containing glass beads. Run 7 used nitrogen in place of carbon monoxide, thus simulating the prior art conditions for the production of "gasoline" from methanol.

TABLE IV

| RUN | 1 | 2 | 3 | 4 | 5 | 6 | 7 | 8 | 9 | 10 | 11 | 12 |
|---|---|---|---|---|---|---|---|---|---|---|---|---|
| CATALYST (g) | A (1 g) | B(1 g) | B (10 g) | B (10 g) | — | E (1 g) | E (1 g) | glass beads | B (10 g) | B (10 g) | B (10 g) | B (10 g) |
| Si/Al$_2$ | 10.0 | 26 | 26 | 26 | — | 23 | 23 | — | 26 | 26 | 26 | 26 |
| Diluent[1] | 9 gm | 9 gm | 0 | 0 | — | 9 | 9 | — | 0 | 0 | 0 | 0 |
| T (°C.) | 355 | 370 | 375 | 375 | 344 | 370 | 375 | 353 | 310 | 372 | 285 | 360 |
| MeOH[2] | 3 | 3 | 1.5 | 3 | 3 | 3 | 3 | 3 | 1.5 | 1.5 | 1.5 | 1.5 |
| WHSV[3] | 2.4 | 2.4 | 0.12 | 0.24 | — | 2.4 | 2.4 | — | 0.12 | 0.12 | 0.12 | 0.12 |
| CO[4] | 1 | 1 | 1 | 1 | 1 | 1 | N$_2$ = 1 | 1 | 1 | 1 | 1 | 1 |
| H$_2$O[5] | 3 | 3 | 1.5 | 0 | 3 | 3 | 3 | 3 | 1.5 | 1.5 | 1.5 | 1.5 |
| CO/MeOH[6] | 33/1 | 33/1 | 66/1 | 33/1 | 33/1 | 33/1 | 33/1 | 33/1 | 66/1 | 66/1 | 66/1 | 66/1 |
| Conversion[7] | 6.3 | 2.5 | 100 | 23 | 0.06 | 24 | 33 | 0.18 | 24 | 40 | 2.7 | 53 |
| Selectivity[8] | 23 | 18 | 4.5 | 9.7 | — | 1.5 | 0.02 | — | 5.2 | 4.5 | 17 | 7.3 |
| Rate[9] | 112 | 330 | 170 | 160 | — | 260 | 18 | — | 38 | 90 | 17 | 13 |
| Abs Acetate[10] | 44 | 9.9 | 68 | 64 | <3 | 7.8 | <3 | <3 | 15 | 27 | 6.7 | 47 |

[1]Diluent = SiO$_2$
[2]ml/hr
[3]gms MeOH/gm catalyst/hr
[4]L (@ STP)/min
[5]ml/hr
[6]moles CO/moles MeOH
[7]moles total product carbon excluding CO incorporation/moles MeOH fed (%)
[8]moles acetic acid + moles methyl acetate/moles total product carbon excluding CO incorporation
[9]moles acetate/gm cat/hr × 10$^6$
[10]measured moles (HOAc + MeOAc) × 10$^4$ From Table IV it can be seen that Runs 1-4, 6 and 9-12 gave conversions and selectivities which were relatively good compared to control Runs 5 and 8 which did not use an H-ZSM-5 catalyst and had conversions of only 0.06% and 0.18%, respectively, and no measurable selectivities. While control Run 7 used an H-ZSM-5 catalyst and had a good conversion of 33%, its selectivity to acetic acid and methyl acetate was about 0% because no carbon monoxide was added. Run 7 gave essentially hydrocarbons. The selectivity to acetic acid and methyl acetate for Runs 1-4, 6 and 9-12 ranged from a low of about 1.5% in Run 6 to a high of about 23% in Run 1. The absolute acetate values (measured moles of acetic acid and methyl acetate × 10$^4$) ranged from 6.7 in Run 11 to 68 in Run 3.

EXAMPLE IV

Runs 13-18 were conducted according to the procedure of Example III using the copper modified catalyst F of Example II. Table V lists the experimental conditions and observed conversion and selectivities. Overall product distributions are given in Table VI for Examples III and IV.

TABLE V

| RUN | 13 | 14 | 15 | 16 | 17 | 18 |
|---|---|---|---|---|---|---|
| CATALYST F (g) | 10 | 10 | 0.98 | 0.98 | 1 | 1 |
| Si/Al$_2$ | 26 | 26 | 26 | 26 | 26 | 26 |
| Diluent[1] | 0 | 0 | 8.8 | 8.8 | 9 | 9 |
| T (°C.) | 362 | 362 | 362 | 361 | 344 | 348 |
| MeOH[2] | 1.5 | 1.5 | 1.5 | 3 | 3 | 3 |
| WHSV[3] | 0.16 | 0.16 | 1.2 | 2.4 | 1.2 | 1.2 |
| CO[4] | 1 | 1 | 1 | 1 | N$_2$ = 0.5 | 0.5 |
| H$_2$O[5] | 1.5 | 1.5 | 1.5 | 3 | 3 | 3 |
| CO/MeOH[6] | 66/1 | 66/1 | 66/1 | 33/1 | 17/1 | 17/1 |
| Conversion[7] | 33 | 18 | 1.3 | 1.5 | 7.3 | 5.8 |
| Selectivity[8] | 17 | 10 | 26 | 32 | 0.4 | 8.4 |
| Rate[9] | 279 | 94 | 103 | 350 | 25 | 533 |
| Abs Acetate[10] | 62 | 28 | 3.6 | 14 | <3 | 16 |

[1]Diluent = SiO$_2$
[2]ml/hr
[3]gms MeOH/gm catalyst/hr
[4]L (@ STP)/min
[5]ml/hr
[6]moles CO/moles MeOH
[7]moles total product carbon excluding CO incorporation/moles MeOH fed (%)

TABLE VI

| | % Selectivities* | | | | | | |
|---|---|---|---|---|---|---|---|
| Run | Acetate | Ethylene | Propane | Propylene | i-Butane | i-Pentane | Other HC |
| 1 | 23 | 24 | 4.6 | 7.4 | 7.9 | 1.9 | 12 |
| 2 | 18 | 32 | 4.1 | 11.0 | 3.4 | 6.2 | 7.1 |
| 3 | 5.0 | 9.6 | 7.4 | 4.8 | 19.2 | 25.2 | 25.1 |
| 4 | 9.7 | 15 | 7.3 | 5.9 | 20 | 20 | 13 |
| 5 | 0 | 0 | 0 | 0 | 0 | 0 | 0 |
| 6 | 1.5 | 30.2 | 9.1 | 24.5 | 11.1 | 14 | 8.7 |
| 7 | 0 | 38 | 7.4 | 16 | 5.9 | 13 | 18 |
| 8 | 0 | 0 | 0 | 0 | 0 | 0 | 0 |
| 9 | 5.2 | 26 | 7.6 | 9.6 | 11 | 25 | 10 |
| 10 | 4.5 | 17 | 11.5 | 6.5 | 27 | 7.3 | 25 |
| 11 | 17 | 32.5 | 2.5 | 11 | 3.5 | 11 | 14 |
| 12 | 7.4 | 16 | 7.5 | 5.1 | 25 | 23 | 15.0 |
| 13 | 17 | 13 | 3.6 | 9.1 | 14 | 15 | 24 |
| 14 | 10 | 22 | 5.2 | 8.9 | 18 | 26 | 4.7 |
| 15 | 26$^a$ | 34 | 14 | 0 | 0 | 0 | 2.5 |
| 16 | 32 | 21 | 6.8 | 0 | 0 | 0 | 15 |
| 17 | 0.4 | 26 | 4.5 | 2.2 | 8.1 | 13 | 45 |
| 18 | 8.4 | 21 | 8.4 | 4.1 | 11 | 20.5 | 22 |

* $\frac{\text{moles product} \times \text{number of MeOH based carbons in molecule}}{\text{total moles product carbon from MeOH}} \times 100$ Acetate selectivities count MeOAc as the productive use of 1 MeOH carbon in the numerator, but as the consumption of 2 moles of MeOH in the denominator. Depending on the ratio of AcOH/MeOAc, deviation in the apparent mass balance from 100% selectivity may be observed.
$^a$Exclusively MeOAc Table V reveals that Runs 13-16 and 18, in which methanol was contacted with carbon monoxide in the presence of H-ZSM-5 catalyst F, which had been impregnated with copper, demonstrated selectivities to acetic acid and methyl acetate ranging from 10% to 32% while control Run 17, in which nitrogen was substituted for carbon monoxide, showed a very low selectivity of about 0.4%. Runs 13 and 14 which used 10 g of undiluted catalyst F and a space velocity of 0.16 WHSV showed the highest conversions but not the highest selectivities. Runs 15 and 16 which used catalyst diluted with silica and a greater space velocity had superior selectivities.

The product stream in the process of this invention contains, in addition to acetic acid and the methyl ester, steam and a hydrocarbon mixture particularly rich in light olefins, especially ethylene. Table VI shows the selectivities of the runs to "acetate" products and various hydrocarbons. It can be seen that Runs 7 and 17 which used nitrogen instead of carbon monoxide are representative of the prior art production of hydrocarbons by contacting methanol with an H-ZSM-5 type zeolite.

It is also apparent from the data in Table VI that the invention provides a process for producing a mixture of acetic acid and ethylene in various proportions and, accordingly, provides a route to vinyl acetate production. Thus methanol and carbon monoxide can serve as the raw materials to yield an acetic acid and ethylene feedstock for making vinyl acetate using known processes.

Further, the invention provides a process for simultaneously producing acetic acid and hydrocarbons in the gasoline ($C_4$-$C_{10}$) boiling range from methanol and carbon monoxide.

EXAMPLE V

The catalyst lifetime is shown by Runs 3, 10 and 12. The catalyst sample in each of these runs was the same and this sample was run daily for one month between Run 3 and Runs 10 and 12 without oxidative regeneration. About 50% catalyst activity was retained.

EXAMPLE VI

In Runs 19-30 the indicated catalyst and methanol were placed in a Hastelloy-C alloy pressure vessel (0.3 liter) and, after establishing a pure carbon monoxide or nitrogen atmosphere, were heated to about 300° C. and 11,000 psig (750 atm). The initial pressure was about 5,000 psig (340 atm) in all the Runs. After an overnight run, the reactor was allowed to cool to room temperature (RT) and the contents were vented slowly through a liquid nitrogen trap. The data in Table VII show the experimental conditions and results. Runs 19-22, 24 and 26 were control runs showing that essentially no reaction occurred unless an H-ZSM-5 type catalyst and carbon monoxide were present.

TABLE VII

| RUN | 19 | 20 | 21 | 22 | 23 | 24 |
|---|---|---|---|---|---|---|
| CONDITIONS | | | | | | |
| CATALYST (g) | NONE | 316 stainless steel shavings 1.11 g | Hastelloy C alloy shavings 1 g | NONE | C 5.02 g | C 4.96 g |
| TEMPERATURE (°C.) | 300 | 300 | 300 | 300 | 300 | 300 |
| METHANOL (g) | 20 | 20 | 20 | 20 | 15.8 | 20 |
| GAS | CO | CO | CO | $N_2$ | CO | $N_2$ |
| FINAL PRESS (psig) | 2,800 RT | 3,600 RT | 3,600 | 6,300 (90° C.) | 4,900 | 6,450 (90° C.) |
| MAXIMUM PRESS (psig) | 11,000 | 11,000 | 11,000 | 11,000 | 10,000 | 10,900 |
| PRODUCTS | | | | | | |
| METHANOL (g) (RECOVERED) | 6.5 | 12.3 | 10.2 | 15.94 | 0 | 0 |
| METHYL FORMATE (g) | 1.14 | 0.28 | 0.30 | 0.022 | 0.98 | 0.04 |
| METHYL ACETATE (g) | 0 | 0.3 | 0.14 | 0.017 | 0.03 | 0.01 |
| ACETONE (g) | 0.16 | 0.11 | 0.01 | 0.093 | 0 | 0 |
| ACETIC ACID (g) | 0 | 0 | 0 | 0 | 2.51 | 0 |
| RUN | 25 | 26 | 27 | 28 | 29 | 30 |
| CONDITIONS | | | | | | |
| CATALYST (g) | D 5.07 g | D 5.05 g | B 3.99 g | F 5.03 g | Erionite/chabazite 5.03 g | H-mordenite 5.01 g |
| TEMPERATURE (°C.) | 300 | 300 | 300 | 300 | 300 | 300 |
| METHANOL (g) | 20 | 0 | 20 | 20 | 20 | 20 |
| GAS | CO | $N_2$ | CO | CO | CO | CO |
| FINAL PRESS (psig) | 6,400 | 6,450 | 4,250 | 4,600 | 3,200 | 4,000 |
| MAXIMUM PRESS (psig) | 10,000 | 11,400 | 10,700 | 10,500 | 10,900 | 10,200 |
| PRODUCTS | | | | | | |
| METHANOL (g) (RECOVERED) | 0.68 | 0.03 | 0.5 | 0.76 | 1.4 | 0.46 |
| METHYL FORMATE (g) | 1.24 | 0.01 | 0.05 | 0.56 | 0.008 | 0 |
| METHYL ACETATE (g) | 0 | 0 | 3.5 | 3.54 | 0.33 | 0.1 |
| ACETONE (g) | 0 | 0 | 0.01 | 0.01 | 0 | 0 |
| ACETIC ACID (g) | 1.31 | 0.11 | 1.2 | 0.68 | 0.02 | 0.06 |

Runs 23, 25, 27 and 28 showed significant yields of acetates. Run 28, which used the copper impregnated catalyst F, indicated that copper apparently has less effect on selectivity at higher pressures. Runs 29 and 30 using erionite/chabazite (1/1) and H-mordenite, respectively, show that zeolites outside the constraint index range of about 1-12 are not as effective for producing the carboxylic acid or the ester derivative.

EXAMPLE VII

In Runs 31-33 acetates were prepared using catalyst B in a procedure similar to Example III. Table VIII shows the experimental conditions and observed conversions and selectivities. Acetates were observed at 300° C. and one atmosphere pressure in Run 31, but only trace amounts were observed when the temperature was increased to 375° C. in Run 32. Increasing the pressure to 1,000 psig (69 atm) in Run 33 again resulted in acetate production.

TABLE VIII

| Run | 31 | 32 | 33 |
|---|---|---|---|
| Catalyst (g) | B (10 g) | B (10 g) | B (10 g) |
| Diluent[1] | 0 | 0 | 0 |
| T (°C.) | 300 | 375 | 375 |
| MeOH[2] | 4.9 | 4.9 | 4.9 |
| WHSV[3] | 0.39 | 0.39 | 0.38 |
| CO[4] | 0.5 | 0.5 | 0.5 |
| H$_2$O[5] | 0 | 0 | 0 |
| CO/MeOH[6] | 10/1 | 10/1 | 10/1 |
| Pressure | 1 atm | 1 atm | 1,000 psig (69 atm) |
| Conversion[7] | 1.3 | 33 | 28 |
| Selectivity[8] | 11.5 | 0 | 1.3 |
| Rate[9] | 19.6 | 3 | 43 |
| Abs. Acetate[10] | 7.5 | <3 | 16 |

[1] Diluent = SiO$_2$
[2] ml/hr
[3] gms MeOH/gm catalyst/hr
[4] L (@ STP)/min
[5] ml/hr
[6] moles CO/moles MeOH
[7] moles total product carbon excluding CO incorporation/moles MeOH fed (%)
[8] moles acetic acid + moles methyl acetate/moles total product carbon excluding CO incorporation
[9] moles acetate/gm cat/hr × 10$^6$
[10] measured moles (HOAc + MeOAc) × 10$^4$

STATEMENT OF INDUSTRIAL APPLICATION

The process of this invention provides a method for preparing acetic acid and methyl acetate by contacting carbon monoxide and methanol with crystalline aluminosilicate zeolites. Acetic acid is a widely used industrial chemical for the manufacture of various acetates such as vinyl acetate, acetyl compounds, cellulose acetate, acetate rayon, and as a solvent for gums, resins and many other substances. Methyl acetate is a useful industrial solvent for nitrocellulose and resins and oils. In addition, by appropriately adjusting the reaction conditions and the amounts of the carbon monoxide and methanol there can be obtained a product stream comprising acetic acid and ethylene in such amounts as to provide a feedstock for the production of vinyl acetate.

I claim:

1. A method for the production of monocarboyxlic acids and esters which comprises contacting carbon monoxide with a monohydric alcohol containing 1 to 4 carbon atoms in the presence of a crystalline aluminosilicate zeolite having a silica to alumina ratio of at least about 6 and a constraint index in the approximate range from 1 to 12, which zeolite does not have rhodium metal dispersed on its surface, in the absence of a halide promoter, under a pressure of at least one atmosphere and at a temperature sufficient to effect a reaction between the carbon monoxide and the alcohol to produce a monocarboxylic acid or ester.

2. In a method for the carbonylation of methanol in the presence of a catalyst, the improvement which comprises reacting carbon monoxide and methanol in the presence of a crystalline aluminosilicate zeolite having a silica to alumina ratio of at least about 6 and a constraint index approximately in the range of 1 to 12, which zeolite does not have rhodium metal dispersed on its surface, in the absence of a halide promoter, under a pressure of at least 1 atmosphere and at a temperature sufficient to effect a reaction between carbon monoxide and methanol to produce acetic acid or methyl acetate.

3. The method of claim 2 wherein ethylene is coproduced.

4. The method of claims 1 or 2 wherein the reaction temperature is from about 200° to 600° C.

5. The method of claim 4 wherein the reaction pressure is about 100 to 20,000 psig.

6. The method of claim 4 wherein the reaction pressure is about 500 to 3,000 psig.

7. The method of claim 4 wherein the carbon monoxide to alcohol molar ratio is from about 1:1 to 1,000:1.

8. The method of claim 7 wherein the alcohol is introduced into the reaction as a mixture with water.

9. The method of claim 8 wherein the volume percent alcohol in the mixture with water ranges from about 10 to 50%.

10. The method of claim 4 wherein the aluminosilicate zeolite has a silica to alumina ratio of about 6 to 150.

11. The method of claim 4 wherein the silica to alumina ratio is at least about 12.

12. The method of claim 4 wherein the aluminosilicate zeolite is H-ZSM-5.

13. The method of claim 4 wherein gasoline is coproduced and recovered.

14. The method of claim 4 wherein the crystalline aluminosilicate zeolite is a ZSM-5 type catalyst.

15. The method of claims 1 or 2 wherein the crystalline aluminosilicate zeolite incorporates by ion exchange a metal of Group IB, IIB, IVB or VIII of the Periodic Table.

16. The method of claims 1 or 2 wherein the crystalline aluminosilicate zeolite incorporates by ion exchange a transition metal capable of forming a carbonyl complex.

17. The method of claim 16 wherein the metal is copper.

18. The method of claim 16 wherein the metal:aluminum molar ratio in the crystalline aluminosilicate zeolite is from 1:100 to 1:1.

19. A method for the preparation of acetic acid or methyl acetate which comprises
   (a) contacting carbon monoxide and methanol in the presence of a crystalline aluminosilicate zeolite having a silica to alumina ratio of at least about 12 and a constraint index approximately from 1 to 12, which zeolite does not have rhodium metal dispersed on its surface, in the absence of a halide promoter, under a pressure of at least 1 atmosphere and at a temperature sufficient to effect a reaction between the carbon monoxide and methanol to produce acetic acid or methyl acetate, and
   (b) recovering the acetic acid or methyl acetate.

20. A method for the production of acetic acid or methyl acetate which comprises
   (a) contacting carbon monoxide and methanol in a molar ratio from about 10:1 to 100:1 in the presence of ZSM-5 zeolite which does not have rhodium metal dispersed on its surface under a pressure ranging from about 500 to 3,000 psig at a temperature from about 200° to 600° C. to produce acetic acid or methyl acetate, and
   (b) recovering the acetic acid or methyl acetate.

* * * * *